United States Patent [19]
Rotolo et al.

[11] Patent Number: 5,480,623
[45] Date of Patent: Jan. 2, 1996

[54] NON-RECIRCULATING COLLECTION SYSTEM FOR STERILIZER EFFLUENT

[75] Inventors: Robert H. Rotolo, Rochester, N.Y.; Charles B. Swenson, Palos Verdes, Calif.; Dale R. Fine, Rochester, N.Y.

[73] Assignee: MDT Corporation, Torrance, Calif.

[21] Appl. No.: 148,465

[22] Filed: Nov. 5, 1993

[51] Int. Cl.⁶ ........................................ A61L 2/20
[52] U.S. Cl. ........................ 422/295; 422/292; 422/298
[58] Field of Search .................. 422/26, 292, 295, 422/298

[56] References Cited

U.S. PATENT DOCUMENTS

| | | | |
|---|---|---|---|
| 3,026,043 | 3/1962 | Lacy et al. | 422/295 |
| 3,107,975 | 10/1963 | Linder | 422/298 |
| 3,717,434 | 2/1973 | Black | 422/298 |
| 3,773,466 | 11/1973 | Linder | 422/295 |
| 3,826,612 | 7/1974 | Black | 422/298 |
| 4,708,849 | 11/1987 | Mielnik, Jr. et al. | 422/298 |
| 5,122,344 | 6/1992 | Schmoegner | 422/298 |
| 5,132,084 | 7/1992 | Harrell et al. | 422/295 |

*Primary Examiner*—Robert J. Warden
*Assistant Examiner*—Theresa T. Snider
*Attorney, Agent, or Firm*—Trask, Britt & Rossa

[57] ABSTRACT

The invention provides a remote non-recirculating steam and condensate collection system for sterilizer effluent. The system includes a cooling tank, apparatus for disposing of collected effluent, and the associated structures which allow for transfer of effluent from the sterilizer into the cooling tank and from the cooling tank to a disposal target. Excess liquid in the cooling tank is disposed of through a simple water displacement technique. An optional waste disposal bottle may periodically be emptied manually.

8 Claims, 1 Drawing Sheet

NON-RECIRCULATING COLLECTION SYSTEM FOR STERILIZER EFFLUENT

BACKGROUND OF THE INVENTION

1. Field

The present invention relates to effluent collection systems. It is particularly directed to remote, non-recirculating steam and condensate collection systems for table top sterilizers.

2. The Art

Medical and dental devices are conventionally sterilized between uses. A particular urgency to provide more effective sterilization procedures has developed with the onset of communicable diseases that are extremely difficult to treat or that have no cure. There is a critical need for apparatus that can be conveniently used for such sterilization on a repeat basis throughout a working day.

Sterilizers can be broadly classified in two groups: plumbed and non-plumbed. Directly plumbed sterilizers are typically large and expensive, while non-plumbed units are smaller and less expensive. The non-plumbed units are generally referred to as "table top" sterilizers, because they are usually of a size to sit on a table or counter top. Table top sterilizers are typically used in office, clinic, and laboratory situations where the larger, directly plumbed, sterilizers are impractical.

Sterilizers in general consist of: a sterilization chamber, a source of sterilant, means for evacuating ambient air from the sterilization chamber and injecting the sterilant, means for heating the sterilant, control means for timing and controlling the sterilization cycle, and exhaust means for removing any remaining sterilant from the sterilization chamber after completion of the sterilization cycle.

Table top sterilizers typically employ liquid sterilants. Liquid sterilants generally comprise water, which may be treated with one or more additives. The liquid sterilant is heated to generate steam for a steam sterilization processes or chemical vapors for chemical vapor sterilization systems. Process control means for the sterilization cycle range from manual operator control to complete automation through the use of electronic controllers, responsive to temperature and pressure sensors.

In plumbed sterilizers, sterilant is continuously available through the plumbing system, and is discharged into the plumbing waste system after each sterilization cycle is completed. Table top sterilizers utilize sterilant source reservoirs that are periodically manually filled with enough sterilant to complete multiple sterilizer cycles. Typically, currently available table top sterilizers are arranged to recirculate sterilant; i.e., effluent is exhausted back to the sterilant source reservoir for recovery after the sterilization cycle is completed. Recovery of the effluent in this manner reduces the frequency of sterilant filling operations required at the sterilant source reservoir.

In existing table top systems, recovered effluent is directed to the lower portion of the sterilant reservoir. Sterilant in the source reservoir provides an efficient means of cooling and condensing the recycled sterilizer effluent for reuse.

Sterilant effluent contains both sterilant and the contaminants removed from the articles being sterilized. Recycling sterilizer effluent to the sterilant source reservoir thus inherently contaminates the sterilant available for the next sterilization cycle. This contamination is a serious matter, especially in light of non-treatable communicable diseases, such as AIDS.

Avoiding recycling of the effluent by merely exhausting the effluent from an unplumbed sterilization chamber to the surrounding atmosphere or to an open drain is not an acceptable option. These practices result in potentially contaminated steam filled work areas for sterilizer operators and any near-by personnel.

There remains a need for a convenient means of collecting and disposing of exhaust from table top sterilizers that will prevent the contaminated effluent from being either recycled or indiscriminately broadcast into the environment.

SUMMARY OF THE INVENTION

This invention provides a non-recirculating collection system for the effluent of sterilizers. Typically, the collection device of this invention is remote from the sterilizer, and comprises a cooling tank and a removable waste bottle. The device is structured and arranged to receive steam exhaust from a sterilizer through appropriate conduit means; e.g., tubing, piping or a hose. Steam and condensate effluent is emitted below the cooling-liquid level in the cooling tank, preferably after being diffused by a suitable fixture associated with the inlet, such as a sintered filter. The effluent is cooled by heat transfer as it mixes with the liquid in the tank.

As effluent is discharged into the cooling tank of the collection device, the liquid level in the tank rises. Eventually, displaced liquid overflows to a storage container, such as a waste disposal bottle. Alternatively, displaced liquid may be routed directly to an external sink or other drain. A waste disposal bottle may be periodically manually emptied or replaced.

A drain port may optionally be provided at the bottom of the cooling tank for convenient draining. This port may be configured as a quick disconnect device. In that event, a length of hose and a quick disconnect coupler may be provided for use in association with the quick disconnect drain port. The hose and quick disconnect coupler may be useful in association with ports mounted at different locations. For example, an alternate overflow drain outlet may be provided at the top of the cooling tank for overflow into a drain, such as a sink.

The waste disposal bottle component of the preferred embodiments interfaces with the cooling tank in a manner allowing displaced liquid to flow into and collect in the disposal bottle. The cooling tank and disposal bottle are structured and arranged to allow easy operator access and removal of the disposal bottle from the cooling tank. A locating structure may be incorporated on the waste disposal bottle. A corresponding mating structure may be situated on the cooling tank or other surface that interfaces with the waste bottle when it is in position during use. Positive assurance that the drain inlet opening in the disposal bottle is correctly positioned under the drain outlet in the cooling tank is provided by the coupled locating and mating structures.

In general, the invention can be regarded as an improvement to table top sterilizer systems of the type in which liquid sterilant is introduced to a sterilization chamber from a sterilant source reservoir, is converted to vapor in the chamber, is withdrawn from the chamber in the vapor state, is introduced as vapor to a pool of liquid coolant comprising liquid sterilant and is condensed within the pool to mix with and become a portion of the cooling liquid.

The improvement generally comprises locating a tank for the cooling liquid separate from the sterilant source reservoir and remote from the sterilization chamber. The tank is structured to include an interior volume configured to provide a vertical travel path upward through liquid contained by the volume. Travel of the vapor through the coolant is generally from an inlet near the bottom of the tank to an outlet near the top of the tank. A fixture associated with the inlet is constructed and arranged to receive vapor. Other structure associated with the outlet functions to direct liquid displaced from the tank to a disposal target. The disposal target may be a container or a drain, for example.

Vapor transfer structure, comprising a flexible conduit such as a pipe or hose, is provided for delivering vapor from the chamber to the tank inlet. The flexible conduit is adapted at one end for connection to a vapor outlet associated with the chamber and adapted at its opposite end for connection to the inlet of the cooling liquid tank.

Suitable liquid receiving means is associated with the disposal target. This means is constructed and arranged to receive liquid displaced from the tank and may constitute the entry to a vessel or drain. According to certain embodiments the target may be a vessel configured to include locating structures adapted to mate with corresponding structures on a surface interfacing with the vessel when the entry is correctly located with respect to the tank outlet.

In summary, the invention provides a remote non-recirculating steam and condensate collection system for sterilizer effluent including a cooling tank, a means of disposing of collected effluent, and the associated structures which allow for transfer of effluent from the sterilizer into the cooling tank and from the cooling tank to a disposal target. Excess liquid in the cooling tank is disposed of through a simple water displacement technique. An optional waste disposal bottle may periodically be emptied manually

BRIEF DESCRIPTION OF THE DRAWINGS

In the drawings, which illustrate what is currently regarded as the best mode for carrying out the invention.

DESCRIPTION OF THE ILLUSTRATED EMBODIMENT

Figure 1:
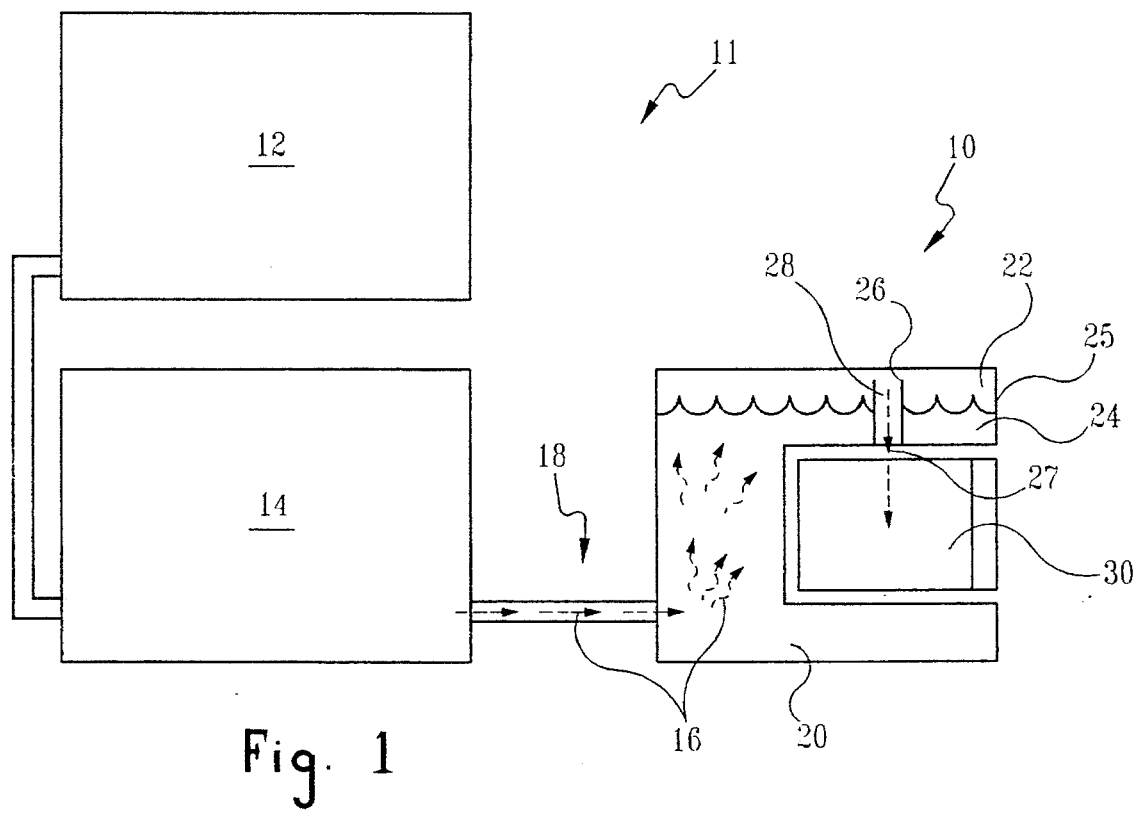
FIG. 1 is a schematic view of a typical table top sterilizer, its associated sterilant supply reservoir, and a remote non-recirculating effluent collection device of the present invention.

A currently preferred embodiment of a non-circulating steam and condensate effluent collection system is designated generally 10. Referring to FIG. 1, a table top sterilizer, designated generally 11, receives liquid from an associated sterilant supply reservoir 12 during the sterilization process. After sterilization is complete, steam and condensate effluent is ejected from the sterilization chamber 14. The flow path of effluent is shown by solid arrows 16 in FIG. 1.

As effluent leaves the sterilization chamber 14, it moves through transfer means, designated generally 18, into the bottom 20 of a cooling tank 22. Hot effluent rises through and mixes with the cooling liquid 24 contained in the cooling tank 22. Liquids in and condensed out of the effluent are incorporated into the body of cooling liquid 24 and cause the liquid level 25 in the cooling tank 22 to rise. Overflow conditions occur as further effluent is added to the cooling liquid 24 after the liquid level 25 rises above the rim 26 of the overflow drain 28. Dashed arrows 27 through the overflow drain 28 illustrate the resulting overflow of excess liquid from the cooling tank 22 into the waste disposal bottle 30.

Figure 2:
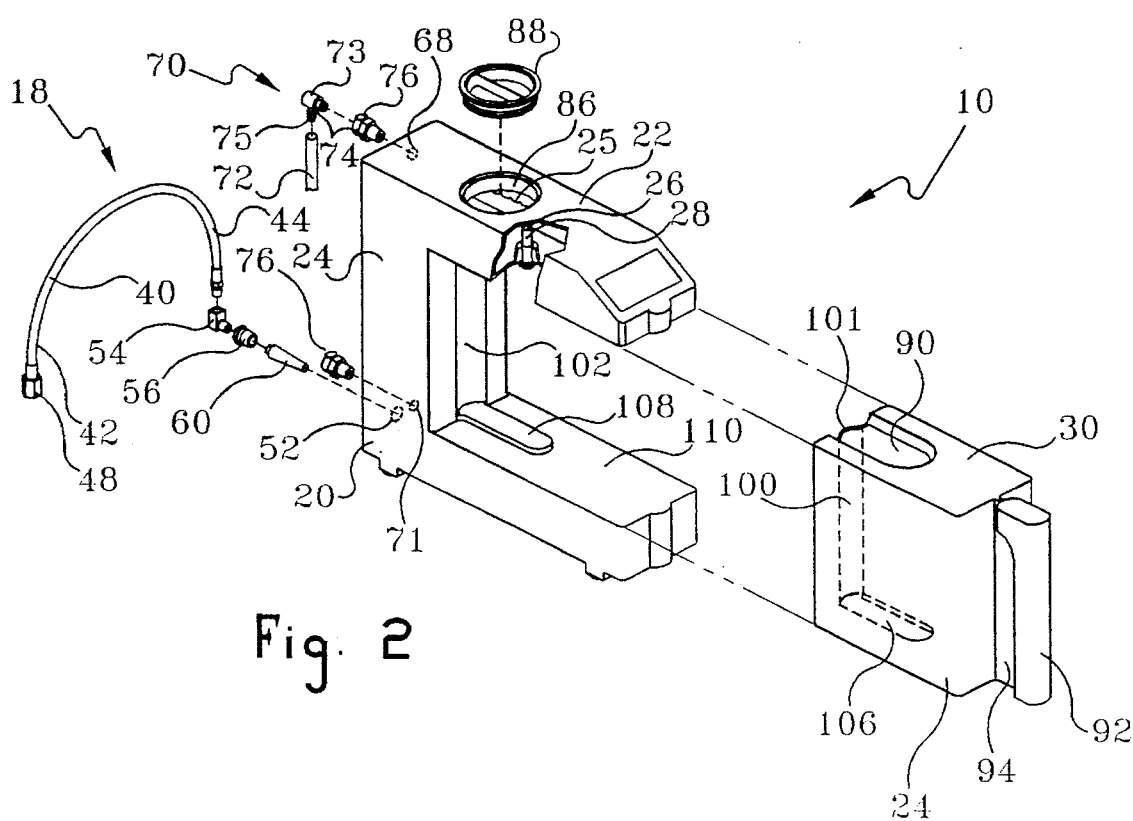
FIG. 2 is an enlarged and exploded view of the effluent collection device of FIG. 1.

Additional details of the non-recirculating collection system of the invention are shown in FIG. 2. Transfer means 18 connecting the sterilizer chamber 14 to the bottom 20 of the cooling tank 22 may include a flexible hose 40 with an inlet end 42 connected to the sterilizer chamber 14 and an outlet end 44 connected to the cooling tank 22. The flexible hose 40 may be constructed of temperature resistant plastics, tough temperature resistant rubber formulations, or articulated metal and lined metal materials, for example. It is presently preferred that the hose 40 be constructed of teflon-lined articulated stainless steel.

A connecter 48 at the inlet end 42 of the hose 40 secures the hose to the exhaust port (not shown) of a table top sterilizer chamber. The connector 48 at the sterilizer chamber 14 may be configured in various ways, but is illustrated as a conventional threaded coupling.

The outlet end 44 of the hose 40 is structurally adapted to the effluent inlet port 52 at the bottom 20 of the cooling tank 22. In the illustrated embodiment, the hose outlet end 44 is attached to a street elbow 54, and is joined through a hex bushing 56 to a filter 60 connected to effluent inlet port 52. A sintered brass filter is currently preferred, but other expedients, such as porous ceramic filters, are also operable. Brass is currently favored for use in construction of the other illustrated fittings, other materials, such as plastic or stainless steel may be equally or more suitable for particular applications.

Effluent is diffused by the filter 60 at the end 44 of the hose assembly 18 prior to being emitted at the bottom 20 (below the cooling-liquid level 25) of the cooling tank 22. Discharging the effluent below the cooling liquid level 25, after first diffusing the steam through the filter 60 assures quiet operation of the system.

The cooling water level is self adjusting, as an overflow drain 28 is positioned in the top of the cooling tank 22 such that the drain rim 26 allows excess liquid in the cooling tank 22 to flow out and collect in the removable waste disposal bottle 30. Alternatively, excess liquid in the cooling tank 22 may be allowed to overflow directly to a sink or other desired drain (not shown) through the use of an alternate overflow drain port 68, also located in the top of cooling tank 22.

A quick disconnecting drain tube assembly, designated generally 70, is provided for use at the alternate overflow drain port 68 and at a cooling tank drain port 71. It is shown in phantom lines at both locations in FIG. 2. The drain tube assembly 70 includes a flow tube 72 fastened to one half 73 of a quick disconnecting coupler 74 by one or more hose barbs 75. A corresponding half 76 of the quick disconnecting coupler 74 is located in each of the alternate overflow drain port 68 and the cooling tank drain port 71. Coupler halves 76 may be permanently installed in the ports 68, 71, or a single such half 76 may be transferrable between these ports with the drain tube assembly 70.

A fill port 86 is provided in the top of the cooling tank 22 to allow the tank to be filled or replenished with cooling liquid 24. A recessed cover 88 for the fill port 86 is removable to allow cleaning access to the cooling tank 22.

The waste disposal bottle 30 is gravity fed from the overflow drain 28 of the cooling tank 22 through a fill opening 90 in the top of the bottle 30. The opening 90 may be any convenient size to receive overflow from the cooling tank. For example: it may be configured to exactly match the outlet of overflow drain 28, or it may consist of the entire top of the bottle 30 in a pitcher configuration. An intermediate size is presently preferred as the simplest means of containing splashing liquids as overflow is added to the existing liquid 24 in the bottle 30.

A handle 92 is provided at an exposed side of the disposal bottle 30 to allow an operator easy access and removal of the disposal bottle from the cooling tank. In the presently preferred embodiment shown in FIG. 2, the handle 92 is defined by indents 94 which are an integral part of a molded bottle 30. Other handle embodiments range from texturized areas such as provided by raised ridges in the area to be gripped, to mechanically attached handles.

In the illustrated embodiment, the waste disposal bottle 30 is keyed to the cooling tank 22 by a raised ridge 100 in the face of the bottle 30, which also provides a pouring lip 101. The raised ridge 100 corresponds to an indentation 102 in a wall of the cooling tank 22. Indented groove 106 in the bottle 30 fits over a raised key 108 in a platform 110 formed by the cooling tank 22. The raised key 110 provides positive assurance that the fill opening 90 in the disposal bottle 30 is correctly positioned under the overflow drain 28 of the cooling tank 22.

While a presently preferred embodiment of the invention has been herein described, it will be apparent that variations are possible within the scope of the appended claims.

What is claimed is:

1. In a table top sterilizer system in which sterilant is introduced to a sterilization chamber, is withdrawn from said chamber in the vapor state and is introduced as vapor to a pool of liquid coolant comprising liquid sterilant, the improvement which comprises:
   a tank for said liquid coolant remote from said sterilization chamber, said tank including:
      an interior volume configured to provide a vertical travel path upward through liquid contained by said volume from an inlet near the bottom of said tank to an outlet near the top of said tank;
      a fixture associated with said inlet constructed and arranged to receive vapor; and
      means associated with said outlet for directing liquid displaced from said tank to a disposal target;
   vapor transfer structure positioned to deliver vapor from said chamber to said inlet; and
   liquid receiving means, associated with said disposal target, constructed and arranged to receive liquid displaced from said tank.

2. An improvement according to claim 1, wherein said disposal target is a vessel with an entry, said entry constituting said liquid receiving means.

3. An improvement according to claim 2, wherein said vessel includes locating structures mating with corresponding structures on a surface of said tank adjacent said vessel when said entry is correctly located with respect to said outlet.

4. An improvement according to claim 1, wherein said vapor transfer structure comprises a flexible conduit, structurally adapted at one end for connection to a vapor outlet associated with said chamber and structurally adapted at its opposite end for connection to said inlet of said tank.

5. An improvement according to claim 1 structured and arranged so that said vapor is condensed within said pool of liquid coolant as said vapor follows said vertical travel path upward through said liquid coolant, and said vapor mixes with and becomes part of said liquid coolant as said vapor condenses, wherein:
   said tank is structured and arranged to align said outlet above said disposal target and said disposal target comprises a vessel with entry means at the top of said vessel;
   a manually operated handle associated with said vessel to facilitate removal of said vessel from under said outlet; and
   said entry means is positively registered, through the use of locating structures positioned on adjacent surfaces of said target and said tank to align said outlet of said tank directly above said entry means of said vessel, whereby excess said liquid coolant may overflow said outlet in said tank, said liquid coolant being gravity fed into said disposal target without connecting structures between said outlet and said entry means.

6. In a table top sterilizer system in which sterilant is stored in a source reservoir, is introduced from said reservoir to a sterilization chamber, is withdrawn from said chamber in the vapor state and is introduced as vapor to a pool of liquid coolant comprising liquid sterilant, the improvement which comprises:
   a tank for said liquid coolant separate from said reservoir and remote from said sterilization chamber, said tank including:
      an interior volume configured to provide a vertical travel path upward through liquid contained by said volume from an inlet near the bottom of said tank to an outlet near the top of said tank;
      a fixture associated with said inlet constructed and arranged to receive vapor; and
      means associated with said outlet for directing liquid displaced from said tank to a disposal target;
   vapor transfer structure positioned to deliver vapor from said chamber to said inlet; and
   liquid receiving means, associated with said disposal target, constructed and arranged to receive liquid displaced from said tank.

7. An improvement according to claim 6, further including:
   a disposal target structured and arranged as a vessel with an entry, said entry constituting said liquid receiving means;
   said vessel further including locating structures structured and arranged to mate with corresponding structures on a surface of said tank adjacent said vessel when said entry is correctly located with respect to said outlet.

8. An improvement according to claim 7, wherein
   said vapor transfer structure comprises a flexible conduit, structurally adapted at one end for connection to a vapor outlet associated with said chamber and structurally adapted at its opposite end for connection to said inlet of said tank.

* * * * *